United States Patent
Faulhaber et al.

[11] 3,937,962
[45] Feb. 10, 1976

[54] CORRECTION OF TWO BEAM PHOTOMETER FOR FLUID ANALYSIS

[75] Inventors: Reimar Faulhaber; Kurt Moldenhauer, both of Frankfurt, Germany

[73] Assignee: Hartmann & Braun Aktiengesellschaft, Frankfurt, Germany

[22] Filed: Nov. 29, 1974

[21] Appl. No.: 528,420

[30] Foreign Application Priority Data
Nov. 30, 1973 Germany............................ 2359637

[52] U.S. Cl. ................. 250/346; 250/351; 356/51; 356/206; 356/222
[51] Int. Cl.² .................. G01N 21/26; G01N 21/36
[58] Field of Search ...... 356/206, 222, 51; 250/343, 250/345, 346, 351

[56] References Cited
UNITED STATES PATENTS
3,700,891  10/1972  Luft ..................................... 250/343
3,725,702  4/1973  Schaefer ............................. 250/343

Primary Examiner—Siegfried H. Grimm
Attorney, Agent, or Firm—Ralf H. Siegemund

[57] ABSTRACT

A two infrared beam gas analyzer, with sample and reference paths and radiation chopper has two absorption cells as detectors wherein the pressures are compared in a first diaphragm capacitor and the sum with parameter modification by operation of pneumatic inpedances is formed in a second diaphragm capacitor. The ratio of the two capacitor outputs constitutes the output of the system. A compact unitary construction is described in detail including the detector chambers and one capacitor in a body serving as mounting element for the second capacitor with a frit like element interposed as pneumatic inpedances and rotational adjustment of that second capacitor as a whole results in parameter adjustment.

8 Claims, 5 Drawing Figures

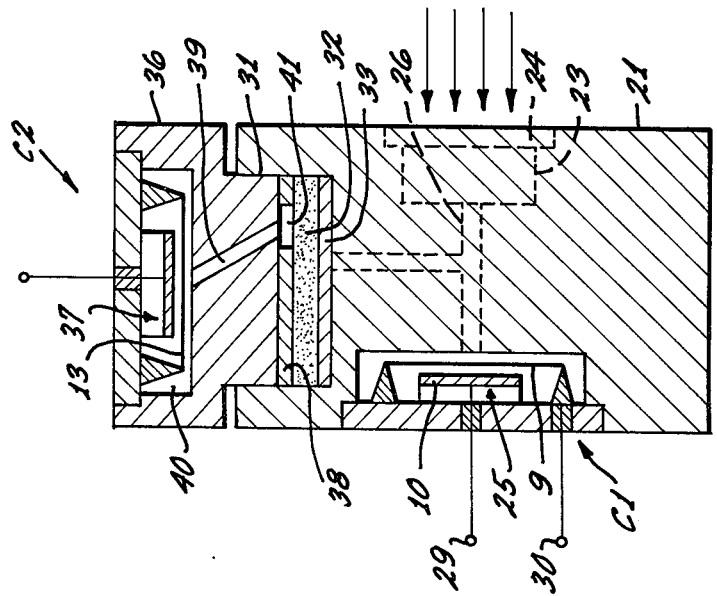
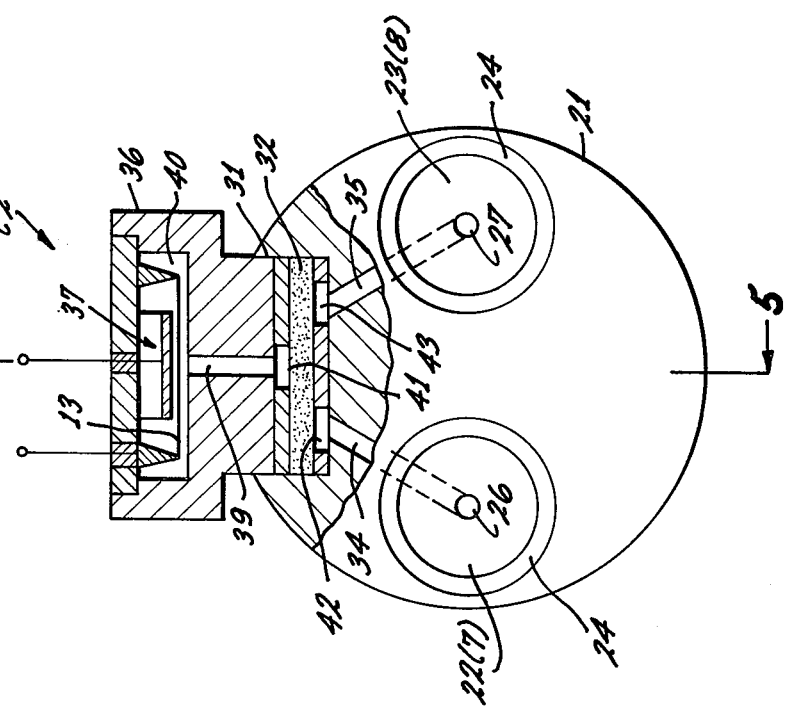

CORRECTION OF TWO BEAM PHOTOMETER FOR FLUID ANALYSIS

BACKGROUND OF THE INVENTION

The present invention relates to correction of a measuring signal being derived from a two beam photometer. Photometers of the type improved by the invention are used for example for fluid analysis. Two beams are derived for example from a single source for radiation, and one beam penetrates a measuring sample (test fluid), while the other beam serves as a reference. The two beams are modulated accordingly and the difference in intensity is detected and measured electrically. A signal is provided accordingly which is proportional to the concentration of a particular constituent in the test fluid.

Two beam photometers as outlined above in general are used for example in gas analysis. The source of radiation provides here particularly radiation which is rich in infrared. In addition to the modulation as established by absorption, the beams are modulated through periodic interception. Also, one uses a pneumatic electric radiation detector which has a gas filled detection chamber for intercepting each beam, and the periodically interrupted beams as absorbed in these chambers produce corresponding pressure variations and pulses. These pressure variations are applied to a diaphragm of a capacitor, and the resulting capacitance variations are electrically detected; they are reflected in a measuring signal representing the pressure difference in the detection chambers, accordingly, that signal is proportional to the beam intensities prior to detection. For a device of this kind, see for example British patent No. 634,453.

It was found that such photometric gas analyzer does not have constant zero or null point and also varies in regards to its sensitivity. Even greatest care in the assembly and operation does not eliminate these variations. As a consequence, a semiautomatic test and calibration apparatus has been developed (see for example German patent 1,548,653) which tests such gas analyzer in predetermined intervals, so that sensitivity and/or zero point can be adjusted; particularly the adjustment is carried out in the amplifier circuit of the instrument. This test equipment is quite extensive and includes gas flow diverter, automatic control and gas adjustment devices.

DESCRIPTION OF THE INVENTION

It is an object of the present invention to improve sensitive stability of a two beam photometer in a less complicated manner, the purpose being in particular the elimination of interferences which affect both beam paths equally.

Interferences are, for example, dust deposits on optical parts in the two beam paths; changes in the radiation emission characteristics of the common source; and sensitivity changes in the electrical equipment and radiation detectors. It should be noted here that interferences affecting both beams and signal paths still distort the output even though symmetry in the construction is observed as to both beam paths because the difference in the two beams as detected is still proportionate to the intensity of either beam. More specifically, the difference in detected beam intensities is equal to or proportional to the product of absorption by sample gas and of the resulting beam intensity in the sample gas path. Variations in the latter for reasons other than a change in absorption still affect the difference as established, even if such variations are tracked by the reference beam.

In accordance with the preferred embodiment of the invention a two beam photometer with measuring beam and reference beam is improved in that the detected intensities of each beam, denoted $I_1$ and $I_2$ are processed, in that a first particular signal K is formed realizing the relation $K = \alpha \cdot I_1 + \beta \cdot I_2$ wherein $\alpha$ and $\beta$ are preselected constant coefficients or parameters both of which are not zero at the same time; and a second particular signal X is formed realizing the relation $X = (I_1 - I_2)/K$. The signal X will then represent the relation $A/(\alpha + \beta(1 - A))$ wherein A is the absorption of and in the sample fluid. Thus, the invention takes into consideration that means are provided to establish a difference signal in representation of $I_2 - I_1$. Now, in addition, a parameter modified sum signal is formed and the ratio X of these two signals is generated.

Under the assumption that all nonselective changes in intensity have the same influence on both individual intensities $I_1$ and $I_2$, this ratio defining signal X is, in effect, the corrected measuring signal which is now free from disturbances in that it is no longer proportionate to any of the intensities $I_1$, $I_2$ individually.

The invention is realized in the following manner. As stated, the basic equipment used is a single radiation source from which two beams are derived, one traversing a cell, cuvette or receptacle as a chamber holding the test fluid, the other beam traversing a cell, cuvette or receptacle as a chamber holding a reference fluid. Both beams are intercepted by absorptioon chambers, and the difference in pressure resulting from absorption is monitored by a capacitor having one electrode constructed as deflectible diaphragm. This equipment is improved in that another diaphragm capacitor has one side of its diaphragm partitioned chamber connected to both radiation detection chambers but via pneumatic impedances. Adjustment in these impedances amounts to selection and variation of the two parameters $\alpha$ and $\beta$ introduced above. The two capacitors are input elements in two individual signal processing channels terminating in a combining circuit that forms the ratio.

Detection chambers, capacitors, and pneumatic impedances can be established in a block with ducts, chambers and attachments to obtain a rather compact and unitary construction, with ease of access for adjustment of the parameters.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 4 is a section view through equipment for practicing the invention; and

FIG. 5 is a section along lines 5—5 in FIG. 4.

Proceeding now to the detailed description of the drawings, FIG. 1 depicts a source 1 of infrared radiation which may be comprised on an electrically heated filament coil. Two beams are branched off and redirected optically into two parallel paths. Reference numerals 2 and 3 denote the necessary optical equipment, known per se, to establish such two beams.

Figure 1:
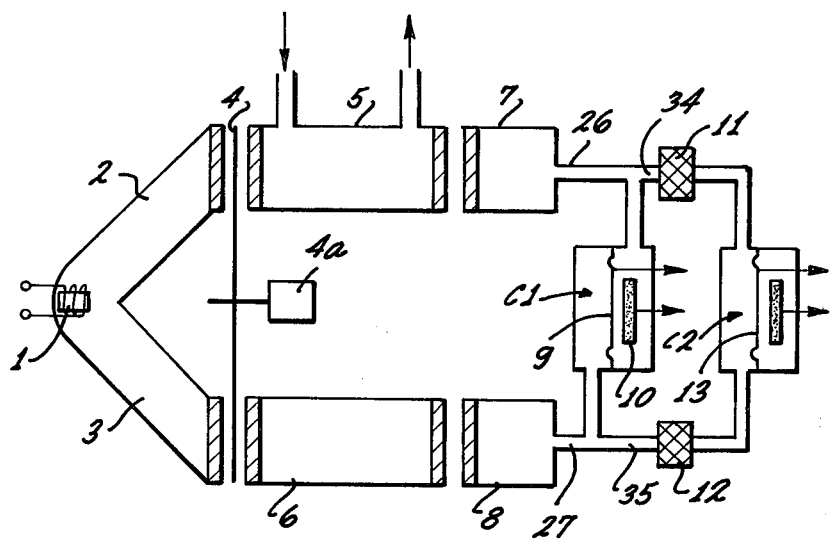
FIG. 1 is a schematic representation of a two beam infrared gas analyzer improved in accordance with the preferred embodiment of the invention.

A slotted disk 4 is driven by a motor 4a and intercepts the two beams for example in phase synchronism. Accordingly, the two beams are periodically interrupted and can be deemed modulated to obtain a carrier frequency.

A first one of the two beams traverses a cell, cuvette or receptacle 5 which is flown through by sample gas on a continuous basis. Specifically, that gas flowing through this sample chamber 5 includes the specific component whose concentration is to be detected on a running basis. The second beam traverses a closed cell, cuvette or receptacle 6 filled with a nonabsorbing gas and serving as a reference chamber. The length $l$ of of the two optical paths through the containers are preferably similar and the material of which they are made is preferably similar.

The two beams as leaving the receptacles 5 and 6 respectively intercept detector chambers 7 and 8, which are filled with the specific gaseous component 1 to be measured. Output ducts 26 and 27, respectively, lead to two entrances in a chamber for a differential pressure capacitor C1.

Capacitor C1 has a first, stationary electrode 10 which can be e.g. bypassed by gas flow. A second capacitor electrode 9 partitions the chamber into two chambers, separately receiving pressure from detector chambers 7 and 8. Electrode 9 is of deflectible diaphragm construction and deflects upon occurrence of a pressure differential at its two sides.

The deflection of electrode 9 varies the effective capacitance of capacitor C1 in representation of different absorption activities in the two detectors. An electrical signal can be derived from the capacitor C1 representing the difference in intensities $I_1$ and $I_2$ of the radiation as intercepted by the two detectors 7 and 8 and converted therein into pressure. If the intensities of the beams as reaching the detection chambers are $I_1$ and $I_2$, the capacitor signal will represent $I_2 - I_1$.

Second duct branches 34 and 35 connect detector chambers 7 and 8 additionally to a second capacitor C2 also having a deflectible diaphragm electrode 13 and a stationary electrode. However, the two ducts terminate on the same side of diaphragm 13. The other subchamber of capacitor C2 is sealed, and subjected to constant pressure. Moreover, pneumatic impedances 11 and 12 are respectively included in the duct paths 34, 35.

As a consequence, diaphragm 13 is deflected in proportion to the expression $\alpha \cdot I_1 + \beta \cdot I_2$, wherein $\alpha$ and $\beta$ are constants (coefficients, parameters) corresponding to the pneumatic impedances 11, 12. $\alpha$ and $\beta$ each have value between 0 and 1, wherein 1 in effect represents zero impedance and 0 represents infinite impedance (i.e., just cut off). It can readily be seen that the ratio of coefficients $\alpha$ and $\beta$ is the decisive aspect here, common factors can be eliminated or are taken care of in further processing of signals. Actually the one of the parameters $\alpha$, $\beta$ can be deemed as being set to 1, the other one being smaller than 1 accordingly. It should be noted, therefore, that impedances 11 and 12 are needed in both branches as a pneumatic short circuit is to be avoided.

It can thus be seen that the two capacitors C1 and C2, upon appropriate bias permit derivation of electrical signals, one being proportionate to $I_1 - I_2$, the other one being proportionate (or equal) to the above defined quantity $K(= \alpha \cdot I_1 + \beta \cdot I_2)$. The circuit shown in FIG. 2 processes these signals further and particularly forms the ratio.

Figure 2:
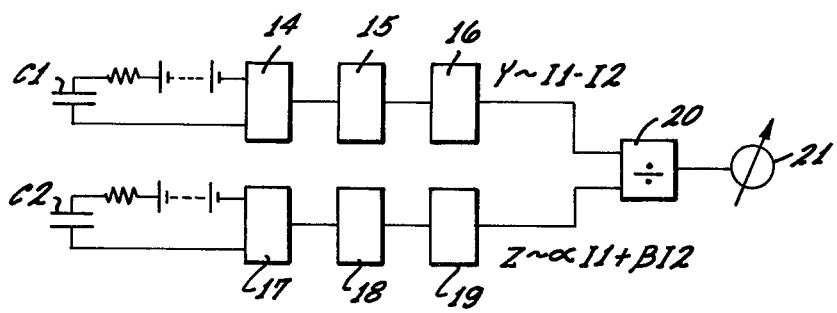
FIG. 2 is a block circuit diagram for processing of signals to be derived from the analyzer shown in FIG. 1.

FIG. 2 shows the two capacitors represented by their electric circuit symbols. The two capacitors each have their own source of dc bias represented by a series circuit connection of a battery and of a resistor. The battery represents merely a suitable source for dc voltage. The capacitors are stimulated periodically and pressure imbalance is superimposed as modulation. The periodically variable voltage as derivable from capacitor C1 is first passed through an amplifier 14, and the amplified signal is rectified in rectifier 15. An electric filter or filter unit 16 smoothes the dc signal which can be termed Y and is proportional to $I_1 - I_2$.

The biased capacitor C2 provides a signal which is likewise amplified in amplifier 17, rectified by a rectifier 18 and filtered in unit 19 to provide for a dc signal which can be termed Z, and which is proportional to $\alpha I_1 + \beta I_2$, wherein one can assume that one of these coefficients ($\alpha, \beta$) is 1 and the other one smaller than 1. Circuit 20 is a signal divider and forms the ratio Y/Z which is (or proportional to) the desired signal X to be constructed. $X = (I_1 - I_2)/K = A/(\alpha + \beta(1-A))$, wherein A represents the absorption by the component to be detected in the sample or test gas passing through a receptacle 5.

In accordance with integration of the well known Lambert — Beer law, there is a particular relation of between absorption A (and, therefore, quantity X as per the relation $X = A/(\alpha + \beta(1-A))$, and the product of concentration C of the measured component and the length $l$ of the optical path through the cell or receptacle 5. The functions and characteristics A (C, $l$) and X (C, $l$) are not linear.

Figure 3:
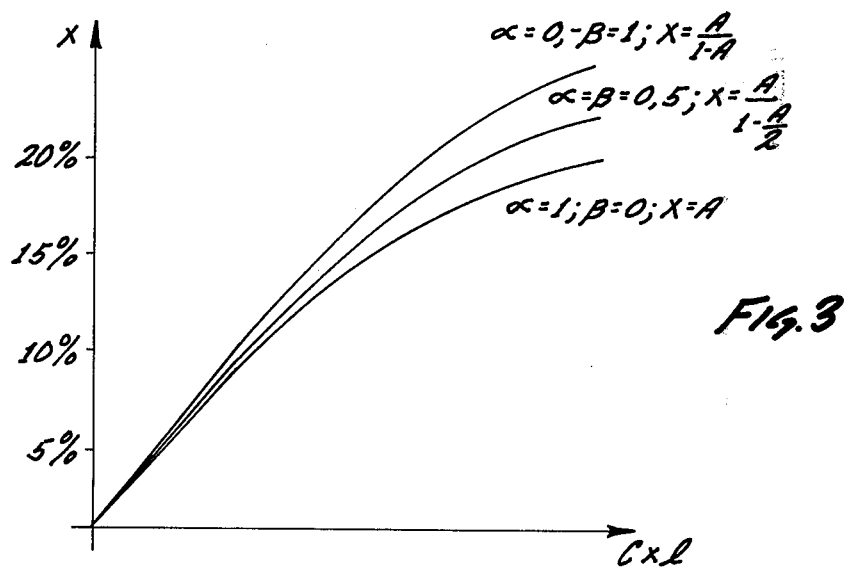
FIG. 3 is a graph showing a family of curves for a corrected measuring signal X as it represents concentration of an constituent in a fluid to be detected.

FIG. 3 shows in particular the resulting functional relation between X and the product C·$l$, in accordance with the Lambert — Beer law, as well as in accordance with the relation above.

The different curves in FIG. 3 result from different parameters $\alpha$ and $\beta$ and are all contained between two characteristics: a first characteristic for $\alpha = 0$, $\beta = 1$ and a second characteristic for $\alpha = 1$ and $\beta = 0$. One can see, that for $\alpha = 0$, $\beta = 1$ the relation above reduces to $X = A/(1 - A)$ and for $\alpha = 1$, $\beta = 0$ $X = A$. The characteristic per se for the latter relation is the one arrived at in prior art devices but without the inventive correction. This particular relation would be arrived at by making impedance 11 infinitely high (i.e., by just eliminating duct 34). Under such circumstnace, one will still have the two capacitors and the two channels, and the corrective funtion is fully effective.

Looking closely at the characteristics one can see that for $\alpha \rightarrow 0$ and $\beta \rightarrow 1$, one obtains a linearization of the characteristic X(C,$l$), in that the linear portion for low values is extended. One can linearize the characteristic further through interpositioning of a non-linear network between ratio forming circuit 20 and instrument 21. Moreover, the indicating instrument 21 as connected to network 20 will be calibrated to eliminate in effect proportionality factors in relations between Y and Z as formed, and $I_1$ and $I_2$ to be represented.

Turning now to structure details as shown in FIGS. 4 and 5, this device permits, particularly, trimming and adjustment (within limits) of the two parameters $\alpha$ and $\beta$. Reference numeral 21 denotes a receiver block 21 having two input chambers 22 and 23 representing in unitary construction the two detectors 7, 8.

The arrows in FIG. 5 denote incoming radiation of the two beams. Each of the chambers is covered by a window 24. Ducts 26 and 27 respectively connect the two chambers 22, 23 to a capacitor chamber 25 partitioned by the diaphragm 9.

Reference numerals 29 and 30 denote the electrical connection to the capacitor C1, one serving directly as output, the other one leading to the series circuit of biasing dc source and resistor as shown in FIG. 2.

The cylindrical block 21 has a recess 31 in which is received a flat frit or frit like, porous body 32 disposed with one side on a gas impermeable foil or seal 33 which covers the bottom of recess 31. These parts are bonded together by a suitable adhesive.

Seal 33 is traversed by two openings respectively above the ends of two branch ducts 34, 35, branching off ducts 26, 27. Therefore, there are defined two entrances for gas respectively from chambers 22, 23 into porous body 32.

A stopper like block 36 closes opening 31 from above and contains the capacitor chamber 37 of the second capacitor C2, with diaphragm electrode 13. The bottom of block 36 is covered by a second foil 38 or seal which is likewise gas impermeable, except for an opening 41. A duct 39 registers with opening 41 and interconnects porous body 32 with one side of the chamber 37 for conduction of gas pressure to that second capacitor.

Accordingly, the two sealing foils 33 and 38 restrict gas flow from ducts 34 and 35 to duct 39 (or to each other), whereby the flow path from 34 to 39 through body 32 establishes the first pneumatic impedance 11 and the flow path through body 32 from 35 to 39 establishes the second pneumatic impedance 12. Ducts 34 and 35 are separated crosswise or transverse through body 32.

Recess 31 as well as the inserted portion of block 36 are of cylindrical configuration, so that block 36 can be turned in recess 31. Accordingly, the disposition opening 41 is varied in relation to openings 42, 43. This change in disposition results in a change in the pneumatic resistance of the two gas paths towards their combining point, which is entrance 41. The drawings show excentric disposition of the openings 42, 43 and 41 in relation to each other. The turning of block 36 accordingly establishes the adjustment function of parameters $\alpha$ and $\beta$.

This particular construction for adjustment does not permit directly adjustment over the full range from $\alpha = 1, \beta = 0$ to $\alpha = 0, \beta = 1$. It was found in practice, however, that this full range is not really needed. In reality, a range from $\alpha = \beta$ up to a dissimilarity ratio of 1:10 well suffices.

The electrodes in capacitor chamber 37 permit connection to external circuit elements to derive therefrom the signal K. Electrodes 29 and 30 permit derivation of a signal proportionate to $I_1 - I_2$ and the circuit of FIG. 2 will then establish signal X.

The invention has been described with reference to an infrared gas analyzer. However, other kinds of radiation can be used where appropriate for the desired analysis, and the invention can also be practiced for liquid analysis. Moreover, the difference signals corresponding to $I_2 - I_1$ and the sum signal $\alpha I_1 + \beta I_2$ can be formed electrically from appropriate outputs of the respective radiation detectors as intercepting the two beams.

The invention is not limited to the embodiments described above but all changes and modifications thereof not constituting departures from the spirit and scope of the invention are intended to be included.

I claim:

1. In a two beam infrared gas analyzer having a first and a second beam of radiation, the first beam traversing sample fluid in a chamber, the second beam traversing a reference fluid in a chamber, a first and second detector respectively for the first and second beams, and first means connected to the first and second detectors to derive therefrom a first signal representing the difference in detected intensities of the beams, the improvement comprising:

second means connected to the first and second detectors to derive therefrom a second signal which is the sum of the products, respectively, of two parameters $\alpha$ and $\beta$ and of the detected intensities; and third means connected to the first and second means for forming the ratios of the first and second signals, said ratio representing directly the relation $A/(\alpha + \beta(1 - A))$, wherein A is the absorption of radiation in the first chamber due to presence of a particular component to be quantitatively detected in said sample fluid.

2. In an analyzer as in claim 1, wherein the first and second detectors respectively include absorption gas chambers, the first means connected to be responsive to differential pressure as between said detector chambers, the second means connected to be responsive to the sum of the pressures in said detector chambers respectively modified by pneumatic impedances in representation of said two parameters.

3. In an analyzer as in claim 2, wherein the first means includes a differential pressure, diaphragm capacitor, and the first and second detector chambers providing pressure variations corresponding to variations in absorption, the second means includes a diaphragm capacitor connected with one and the same side to said detector chambers respectively via said pneumatic impedances.

4. In a gas analyzer as in claim 2, wherein the pneumatic resistances are established by paths through porous, outwardly sealed material.

5. In a gas analyzer as in claim 4, wherein the material is a porous body with two connections to the two detector chambers and a third connection to said diaphragm capacitor of said second means.

6. In a gas analyzer as in claim 5, said body being a frit or a frit like body.

7. In a gas analyzer as in claim 1, and including a first body with two chambers as said detector chambers, each chamber having a window, a first capacitor chamber in the first body with a diaphragm as one electrode partitioning the chamber; ducts in the first body connecting the chamber at opposite sides of said diaphragm to said two chambers; the first body having a recess receiving a second body of porous material, a pair of ducts in said first body connecting the two chambers respectively to the recess; the second means including means defining a second capacitor chamber with diaphragm and being disposed in the recess so that one side of the diaphragm communicates with the ducts of the pair through the second body of porous material.

8. In an analyzer as in claim 7, the means defining a second capacitor chamber being an insert rotatably disposed in said recess for adjustment of the travel path of gas from the ducts of the pair through the second, porous body to the one side of the diaphragm of the second capacitor.

* * * * *